United States Patent
Pedicini

(10) Patent No.: US 11,134,962 B2
(45) Date of Patent: *Oct. 5, 2021

(54) ORTHOPEDIC IMPACTING DEVICE HAVING A LAUNCHED MASS DELIVERING A CONTROLLED, REPEATABLE AND REVERSIBLE IMPACTING FORCE

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/600,284

(22) Filed: May 19, 2017

(65) Prior Publication Data

US 2018/0055554 A1    Mar. 1, 2018

Related U.S. Application Data

(63) Continuation of application No. 15/439,692, filed on Feb. 22, 2017, now Pat. No. 10,603,050.

(Continued)

(51) Int. Cl.
*A61B 17/92*    (2006.01)
*A61B 17/16*    (2006.01)
(Continued)

(52) U.S. Cl.
CPC ...... *A61B 17/1628* (2013.01); *A61B 17/1604* (2013.01); *A61B 17/1655* (2013.01);
(Continued)

(58) Field of Classification Search
None
See application file for complete search history.

(56) References Cited

U.S. PATENT DOCUMENTS

| 4,468,594 A | 8/1984 | Jacquemet |
| 5,057,112 A | 10/1991 | Sherman et al. |

(Continued)

FOREIGN PATENT DOCUMENTS

| JP | 2004130471 A | 4/2004 |
| JP | 2006512149 A | 4/2006 |
| WO | 2016/112397 A1 | 7/2016 |

OTHER PUBLICATIONS

International Search Report and Written Opinion issued in Application No. PCT/US2017/018921 dated May 29, 2017.

(Continued)

*Primary Examiner* — Samuel S Hanna

(57) ABSTRACT

A motor-driven orthopedic impacting tool is provided for orthopedic impacting in the hips, knees, shoulders and the like. The tool is capable of holding a broach, chisel, or other end effector, which when gently tapped in a cavity with controlled percussive impacts, can expand the size or volume of an opening of the cavity or facilitate removal of the broach, implant, or other surgical implement from the opening. A stored-energy drive mechanism stores potential energy and then releases it to launch a launched mass or striker to communicate a striking force to an adapter in either a forward or reverse direction. The tool may further include a combination anvil and adapter and an energy adjustment mechanism to adjust the striking force the launched mass delivers to the adapter in accordance with a patient profile.

32 Claims, 9 Drawing Sheets

Related U.S. Application Data

(60) Provisional application No. 62/381,864, filed on Aug. 31, 2016.

(51) Int. Cl.
*A61F 2/46* (2006.01)
*A61B 90/30* (2016.01)
*A61B 17/17* (2006.01)
*A61B 90/00* (2016.01)
*A61B 17/00* (2006.01)

(52) U.S. Cl.
CPC .............. *A61B 17/17* (2013.01); *A61B 17/92* (2013.01); *A61B 90/30* (2016.02); *A61F 2/4603* (2013.01); *A61B 2017/00022* (2013.01); *A61B 2017/00137* (2013.01); *A61B 2017/00398* (2013.01); *A61B 2017/00473* (2013.01); *A61B 2017/00477* (2013.01); *A61B 2017/00734* (2013.01); *A61B 2017/924* (2013.01); *A61B 2090/0807* (2016.02)

(56) References Cited

U.S. PATENT DOCUMENTS

| | | | |
|---|---|---|---|
| 5,108,400 A | 4/1992 | Appel et al. | |
| 5,992,538 A | 11/1999 | Marcengill et al. | |
| 6,199,640 B1 * | 3/2001 | Hecht | B25D 16/00 173/109 |
| 6,387,113 B1 | 5/2002 | Hawkins et al. | |
| 6,875,220 B2 | 4/2005 | Du et al. | |
| 6,938,705 B2 | 9/2005 | Kikuchi | |
| 8,602,124 B2 | 12/2013 | Pedicini | |
| 8,695,726 B2 | 4/2014 | Pedicini | |
| 8,936,105 B2 | 1/2015 | Pedicini | |
| 9,539,714 B1 | 1/2017 | Pedicini | |
| 9,901,354 B2 | 2/2018 | Pedicini | |
| 9,950,417 B2 * | 4/2018 | Ito | B25F 5/00 |
| 9,962,821 B2 | 5/2018 | Pedicini et al. | |
| RE46,954 E | 7/2018 | Pedicini | |
| RE46,979 E | 8/2018 | Pedicini | |
| 10,065,300 B2 | 9/2018 | Pedicini | |
| 10,603,050 B2 | 3/2020 | Pedicini | |
| 10,751,865 B2 | 8/2020 | Pedicini et al. | |
| 2004/0026097 A1 * | 2/2004 | Hecht | B25D 11/005 173/114 |
| 2005/0101962 A1 | 5/2005 | Schwenke et al. | |
| 2005/0247462 A1 | 11/2005 | Meixner et al. | |
| 2008/0245541 A1 | 10/2008 | Grunig | |
| 2009/0236387 A1 | 9/2009 | Simonelli et al. | |
| 2009/0266570 A1 | 10/2009 | Hashimoto et al. | |
| 2010/0137760 A1 | 6/2010 | Schulz et al. | |
| 2012/0215267 A1 | 8/2012 | Pedicini | |
| 2013/0161050 A1 * | 6/2013 | Pedicini | B25D 17/00 173/201 |
| 2014/0318819 A1 | 10/2014 | Pedicini | |
| 2015/0196343 A1 | 7/2015 | Donald et al. | |
| 2015/0289886 A1 * | 10/2015 | Kfir | A61B 17/1604 606/84 |
| 2016/0096259 A1 | 4/2016 | Pedicini | |
| 2016/0199199 A1 | 7/2016 | Pedicini | |
| 2017/0042692 A1 | 2/2017 | Stewart et al. | |
| 2017/0196701 A1 | 7/2017 | Behzadi et al. | |
| 2018/0055518 A1 | 3/2018 | Pedicini | |
| 2018/0055552 A1 | 3/2018 | Pedicini | |
| 2018/0055553 A1 | 3/2018 | Pedicini | |
| 2020/0197028 A1 | 6/2020 | Pedicini | |

OTHER PUBLICATIONS

International Search Report and Written Opinion dated Jun. 8, 2017 in PCT/US2017/020218.
Yanoso-Scholl et al.; A Novel Test Method to Characterize Intraoperative Impacts During Femoral Broaching and Stem Insertion, ORS 2012 Annual mtg. (1 page).
U.S. Appl. No. 17/367,875, filed Jul. 6, 2021, Christopher Pedicini.

* cited by examiner

ORTHOPEDIC IMPACTING DEVICE HAVING A LAUNCHED MASS DELIVERING A CONTROLLED, REPEATABLE AND REVERSIBLE IMPACTING FORCE

CROSS REFERENCE TO RELATED APPLICATIONS

This application is a continuation of U.S. patent application Ser. No. 15/439,692 filed Feb. 22, 2017, the entire contents of which is incorporated herein by reference. application Ser. No. 15/439,692 is based on and claims the benefit of 35 USC § 119 to U.S. Provisional Patent Application No. 62/381,864 filed Aug. 31, 2016.

The present disclosure relates to locally powered tools for impacting in surgical applications such as orthopedic procedures, and, more particularly, to a hand-held motor driven tool for bidirectional, surgical impacting that is driven by a launched mass to provide controlled, repeatable impacts to a broach or other end effector.

BACKGROUND

In the field of orthopedics, prosthetic devices, such as artificial joints, are often implanted or seated in a patient's bone cavity. The cavity is typically formed during surgery before a prosthesis is seated or implanted, for example, a physician may remove and or compact existing bone to form the cavity. The prosthesis usually includes a stem or other protrusion that is inserted into the cavity.

To create the cavity, a physician may use a broach conforming to the shape of the stem of the prosthesis. Solutions known in the art include providing a handle with the broach for manual hammering by the physician during surgery to impel the broach into the implant area. Unfortunately, this approach is crude and notoriously imprecise, leading to unnecessary mechanical stress on the bone and highly unpredictable depending upon the skill of a particular physician. Historically, this brute force approach will in many cases result in inaccuracies in the location and configuration of the cavity. Additionally, the surgeon is required to expend an unusual amount of physical force and energy to hammer the broach and to manipulate the bones and prosthesis. Most importantly, this approach carries with it the risk that the physician will cause unnecessary further trauma to the surgical area and damage otherwise healthy tissue, bone structure and the like.

Another technique for creating the prosthetic cavity is to drive the broach pneumatically, that is, by compressed air. This approach is disadvantageous in that it prevents portability of an impacting tool, for instance, because of the presence of a tethering air-line, air being exhausted from a tool into the sterile operating field and fatigue of the physician operating the tool. This approach, as exemplified in U.S. Pat. No. 5,057,112 does not allow for precise control of the impact force or frequency and instead functions very much like a jackhammer when actuated. Again, this lack of any measure of precise control makes accurate broaching of the cavity more difficult, and leads to unnecessary patient complications and trauma.

A third technique relies on computer-controlled robotic arms for creating the cavity. While this approach overcomes the fatiguing and accuracy issues, it suffers from having a very high capital cost and additionally removes the tactile feedback that a surgeon can get from a manual approach.

A fourth technique relies on the inventor's own, previous work which uses a linear compressor to compress air on a single stroke basis and then, after a sufficient pressure is created, to release the air through a valve and onto a striker. This then forces the striker to travel down a guide tube and impact an anvil, which holds the broach and or other surgical tool. However, this arrangement, due to the pressure of the air, results in the generation of large forces on the gear train and linear motion converter components, which large forces lead to premature wear on components.

Consequently, there exists a need for an impacting tool having an improved drive assembly that overcomes the various disadvantages of existing systems and previous solutions of the inventor.

SUMMARY

In view of the foregoing disadvantages, an electric motor-driven orthopedic impacting tool is provided for orthopedic impacting in hips, knees, shoulders and the like. The tool is capable of holding a broach, chisel, or other end effector and gently tapping the broach, chisel or other end effector into the cavity with controlled percussive impacts, resulting in a better fit for the prosthesis or the implant. Further, the control afforded by such an electrically manipulated broach, chisel, or other end effector allows adjustment of the impact settings according to a particular bone type or other profile of a patient. The tool additionally enables proper seating and in the case of bidirectional movement the removal of the prosthesis or the implant into or out of an implant cavity and advantageously augments the existing surgeon's skill in guiding the instrument.

In an exemplary embodiment, an electric motor-driven orthopedic impacting tool comprises a local power source (such as a battery or fuel cell), a motor, a controller, a housing, a method of converting rotary motion to linear motion (hereafter referred to as a linear motion converter), a stored-energy drive system or mechanism such as a gas or mechanical spring capable of storing and releasing potential energy, and a striker energized by the stored-energy drive system to be operational in a forward and/or a rearward direction, where the striker is capable of generating an impact force to a surgical implement. The tool may further deliver focused illumination to the surgery area by way of a semiconductor light source, such as an LED, or traditional incandescent light source. A handle may be provided for handling the tool by a physician, or a suitable mount interface for integrating the tool into a robotic assembly. A local power source such as a battery is also included. As is typical, at least some of the various components are preferably contained within a housing. The tool is capable of applying cyclic, repeatable impact forces on a broach, chisel, or other end effector, or an implant. Given the repeatability of the impact force, finely tuning the impact force to a plurality of levels is also contemplated. To this end a plurality of gas springs may be provided together with the device in a kit format, whereby different color-coded gas springs may be removably introduced to the tool as needed during a surgical procedure to provide for a range of drive forces.

Regarding the stored-energy drive system, the system is preferably actuatable by a motor and gearbox in combination with a cam, which rotates in a first direction compressing a spring, thus storing potential energy within the stored-energy drive system. The cam further continues to rotate and releases the stored energy, which, in turn, can accelerate itself or another mass to generate a forward impact force as a drive assembly. As an example, after sufficient displacement of a mechanical spring or gas spring, in which stored potential energy is increased, the cam continues to rotate until it moves past a release point where it ceases to act on the mass, releasing the stored energy. Upon release, the energy or, more preferably, other mass is accelerated in the forward direction by the stored-energy drive system until it comes into operative contact with the point of impact, such as the anvil or another impact surface. Conversely, for a bidirectional impacting system the cam can alternatively rotate in an opposite, second direction, compressing a spring, again storing potential energy within the spring storage system. The cam further continues to rotate to a release point where it ceases to act on the spring storage system and the spring storage system can release the stored energy, which, in turn, can accelerate itself or another mass to generate a rearward impact force. As an example, after sufficient displacement of the spring, in which stored potential energy of the spring/gas spring is increased, the cam continues to rotate until it moves past a release point where it ceases to act on the mass, releasing the stored-energy drive system (or mechanism). Upon release, the stored-energy drive system or other mass is accelerated in the opposite, rearward direction by the stored-energy drive system until it comes into operative contact with the point of impact, such as the anvil or another impact surface.

In an exemplary embodiment, the launched mass (which can be the stored-energy drive system itself) separates from a pusher plate or pushing surface prior to its point of impact. Accordingly, in this embodiment, since the entire stored-energy drive system is the launched mass very high efficiencies were unexpectedly achieved. In a further embodiment which uses a mechanical spring, the compression ratio of the spring is less than about 50% of its free length, which the inventor has found reduces the likelihood of permanent spring deformation.

In a further exemplary embodiment, the handle may be repositionable or foldable back to the tool to present an inline tool wherein the surgeon pushes or pulls on the tool co-linearly with the direction of the broach. This has the advantage of limiting the amount of torque the surgeon may put on the tool while it is in operation. In a further refinement of the hand grip, there may be an additional hand grip for guiding the surgical instrument and providing increased stability during the impacting operation. In a still further embodiment, the tool may be attached to a robot thus eliminating the need for a handle and the tool may use a tethered or remote power source.

In a further exemplary embodiment, the broach, chisel or other end effector can be rotated to a number of positions while still maintaining axial alignment. This facilitates the use of the broach for various anatomical presentations during surgery.

In a further exemplary embodiment, the tool further comprises a control element or controller, which includes an energy adjustment element or mechanism, and which energy adjustment element may control the impact force of the tool by controlling storage and release of energy output from the stored-energy drive mechanism. The energy may be regulated electronically or mechanically. Furthermore, the energy adjustment element may be analog or have fixed settings. This control element allows for the precise control of the impacting operation. The energy adjustment element allows a surgeon to increase or decrease the impact energy of the tool according to a patient's profile.

In an exemplary embodiment, an anvil of the tool includes at least one of two points of impact, a forward striking surface or first surface and a rearward striking surface or second surface, and a guide assembly, such as guide rollers, bearings, or Polytetrafluoroethylene (PTFE) or Teflon tracks to constrain the striker to move in a substantially axial direction. The point of impact of the striker and the resulting force on the surgical tool can be both in the forward and reverse directions. In the bidirectional impacting operation, when a forward force on the surgical tool is generated, the striker moves along the guide assembly and continues in the forward direction. A reversing mechanism can be used to change the point of impact of the striker and the resulting force on the surgical tool. Use of such a reversing mechanism results in a rearward force being exerted on the anvil and/or the broach or other surgical attachment. As used in this context, "forward direction" connotes movement of the striker toward a broach, chisel or patient, and "rearward direction" connotes movement of the striker away from the broach, chisel or patient. The selectivity of either bidirectional or unidirectional impacting provides flexibility to a surgeon in either cutting or compressing material within the implant cavity in that the choice of material removal or material compaction is often a critical decision in a surgical procedure, as discussed, for example, in U.S. Pat. No. 8,602,124. Furthermore, it was discovered in the use of the inventor's own, previous work that the tool could be used in a broader range of surgical procedures if the reverse impact force could be approximately equal to the forward impact force. In an embodiment the forward and rearward forces impact at least two separate and distinct points.

In an exemplary embodiment the anvil and the adapter comprise a single element, or one may be integral to the other.

In an exemplary embodiment the tool is further capable of regulating the frequency of the striker's impacting movement. By regulating the frequency of the striker, the tool may, for example, impart a greater total time-weighted percussive impact, while maintaining the same impact magnitude. This allows for the surgeon to control the cutting speed of the broach or chisel. For example, the surgeon may choose cutting at a faster rate (higher frequency impacting) during the bulk of the broach or chisel movement and then slow the cutting rate as the broach or chisel approaches a desired depth. In typical impactors, as shown in U.S. Pat. No. 6,938,705, as used in demolition work, varying the speed varies the impact force, making it impossible to maintain constant (defined as +/−40%) impact energy in variable speed operation.

In an exemplary embodiment the direction of impacting is controlled by a biasing force placed by a user on the tool and detected by a sensor, such as a positioner sensor, on the anvil. For example, biasing the tool in the forward direction results in the launched mass being launched forward and gives forward impacting, whereas biasing the tool in the rearward direction results in the launched mass being launched rearward and gives rearward impacting.

In an exemplary embodiment the tool may have a lighting element to illuminate a work area and accurately position the broach, chisel, or other end effector on a desired location on the prosthesis or the implant.

In an exemplary embodiment a bumper is predisposed between a head of the piston and an end of the striker, reducing the impact stress and prolonging the life of the entire assembly.

In an exemplary embodiment the tool may also include a feedback system that warns the user when a bending or off-line orientation beyond a certain magnitude is detected at a broach, chisel, or other end effector or implant interface or the orthopedic implement is not advancing.

In an exemplary embodiment the tool may further allow for a replaceable cartridge to vary the impact forces. These cartridges could be rated by the total energy delivered by the stored energy system when actuated by the linear motion converter. As an example, a low power cartridge with a limit in the range of 2 to 3 joules or less could be used for soft or osteoporotic bone. In the case of young, hard bone, a power cartridge with impact energy of 4 to 5 joules could be selected. By allowing for a variety of cartridges, which in an embodiment could be color coded according to power, the surgeon would have flexibility in determining the impact energy to apply by simply selecting the appropriate power cartridge provided with the tool in a kit.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific non-limiting objects attained by its uses, reference should be made to the accompanying drawings and detailed description in which there are illustrated and described exemplary embodiments of the present disclosure.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

A motor-driven orthopedic impacting tool is provided with controlled percussive impacts. The motor may be electric, such as a brushless, autoclavable motor such as those generally available from Maxon Motor® and/or Portescap®. The tool includes the capability to perform single and multiple impacts, as well as impacting of variable and varying directions, forces, and frequencies. In an embodiment the impact energy is adjustable. In another embodiment the impact is transferred to a broach, chisel, or other end effector connected to the tool.

The tool further includes a housing. The housing may securely cover and hold at least one component of the tool and is formed of a material suitable for surgical applications, such as aluminum or Polyphenylsulfone (PPSF or PPSU), also known as Radel®. In an embodiment, the housing contains a motor, at least one reducing gear, a linear motion converter, a spring element which is preferably a mechanical or gas spring, a striker or launched mass, a control circuit or module, an anvil, a first or forward striking surface for forward impact, and a different, second or rearward striking surface for rearward impact.

The tool further may include a handle portion with an optional hand grip for comfortable and secure holding of the tool, or a suitable mount interface for integrating the tool into a robotic assembly while in use, and an adapter, a battery, a positional sensor, a directional sensor, and a torsional sensor. The tool may further deliver focused illumination by way of a semiconductor light source, such as an LED, or traditional incandescent light source to provide light in the surgical work area in which a surgeon employs the tool. The anvil may be coupled to a broach, chisel or other end effector known in the art through the use of an interfacing adapter, which adapter may have a quick connect mechanism to facilitate rapid change of different broaching sizes. The anvil may further include a locking rotational feature to allow the tool to be positioned in different fashions as to gain tissue clearance to tool features such as the handle.

Figure 1:
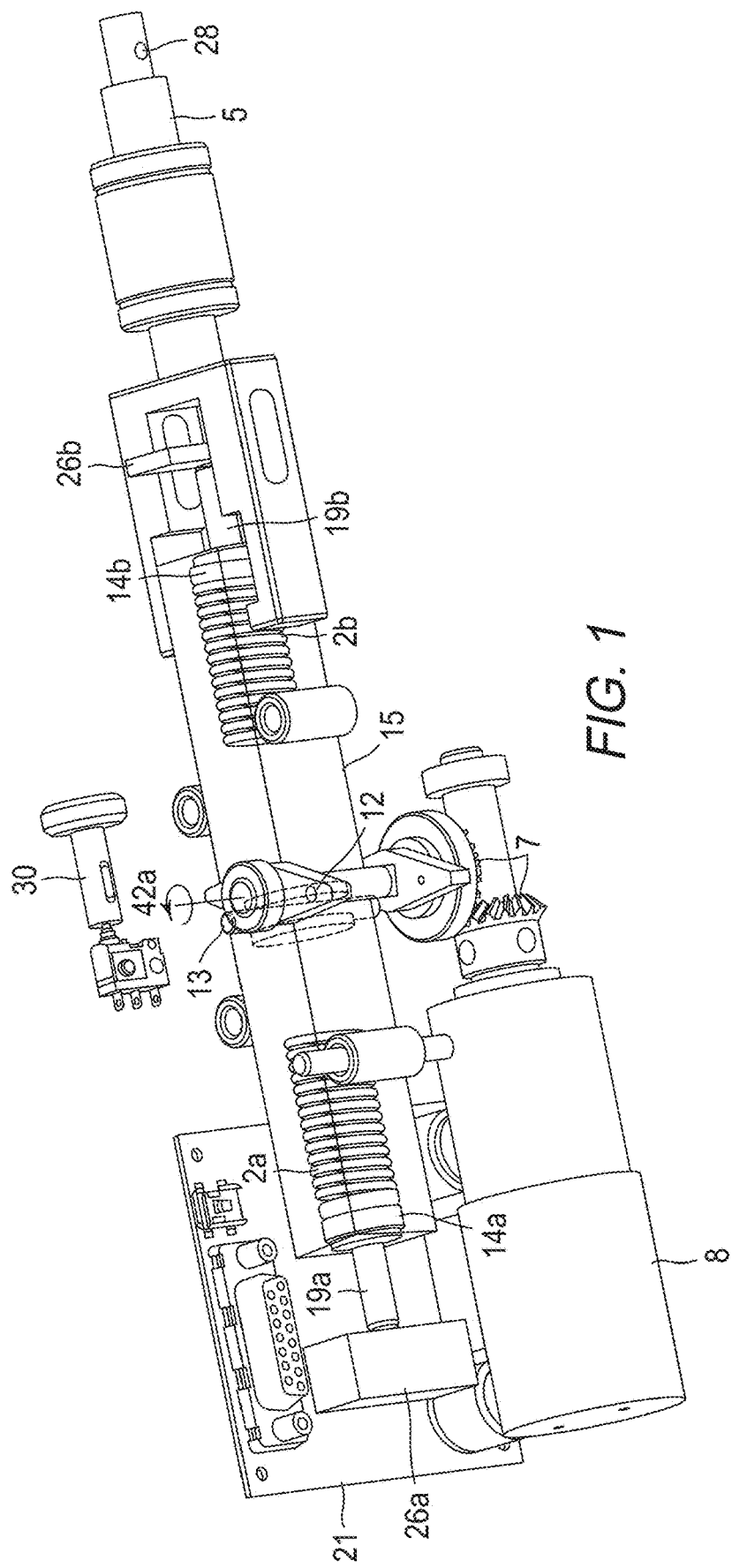
FIG. 1 illustrates a perspective view of an orthopedic impacting tool in accordance with an exemplary embodiment of the present disclosure in which a mechanical spring assembly system is used for generating a forward impact force.

Referring now generally to FIGS. 1 through 7, in an exemplary embodiment, a bidirectional impact force may be generated using a dual mechanical spring assembly system, as illustrated, for example, in FIG. 1. Alternatively, a single mechanical spring assembly may be used. FIG. 1 shows a perspective view of an orthopedic impacting tool in accordance with an embodiment of the present disclosure in which a motor and gearbox 8 of the mechanical spring assembly system, in combination with a linear motion converter, which includes a cam 12 and a cam follower 13, actuates a first spring piston 19a (hereinafter referred to as the "first piston 19a") and/or a launched mass or striker 15, in order to ultimately generate a forward impact force. It is to be noted that the piston generally refers to a thrusting or push off element and can have any of a number of shapes. The cam 12 is shown as having a symmetrical profile, a dual wedge shape, but the design contemplates that any shape may be used which provides a quick release of the spring. Alternative ways for actuating and quickly releasing the spring include, but are not limited to, using an interrupted rack and pinion or a climbing mechanism. The spring assembly system further includes, among other components, reducing gears 7 and an anvil 5. The first piston 19a engages a first spring 2a, which can be either a mechanical or gas spring. In the mechanical spring assembly system, the deflection in relation to a free length of the spring is preferably less than 50%. Music wire or, more preferably, stainless steel or titanium are suitable materials for the spring. Preferably, the spring is a compression spring, although other types of springs are contemplated. In the gas spring assembly system, the gas spring operates under pressure in a range of about 100 to 3000 psi, for example. The gas spring is preferably initially charged with a non-oxidizing gas, such as nitrogen, or an inert gas, such as argon. One of the advantages of using nitrogen can include a lower permeation rate through seals of the gas spring, resulting in a potentially longer shelf life for the seals and the spring itself.

Figure 2:
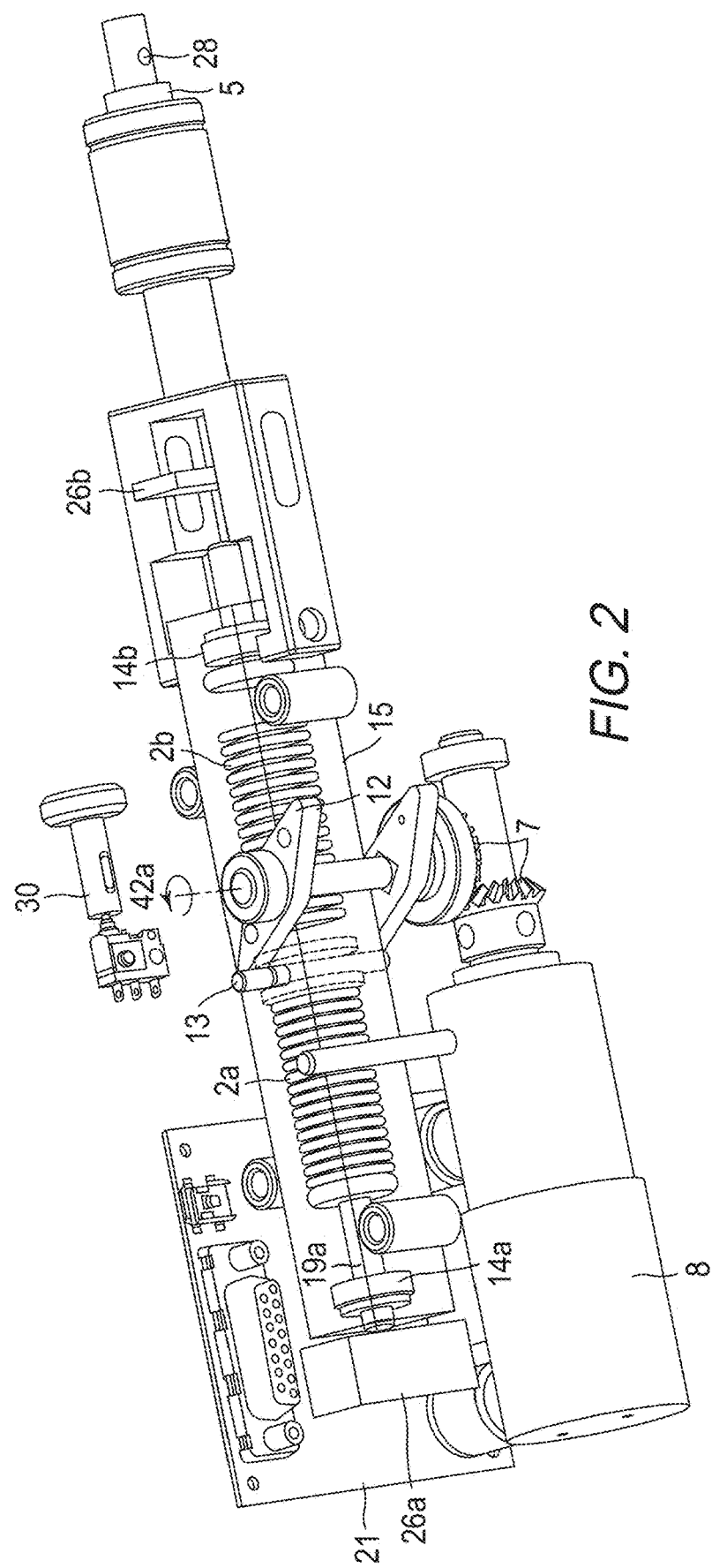
FIG. 2 shows an exemplary embodiment of the tool in FIG. 1 in which the cam positions the piston in the operative position for release for a forward impact.
Figure 3:
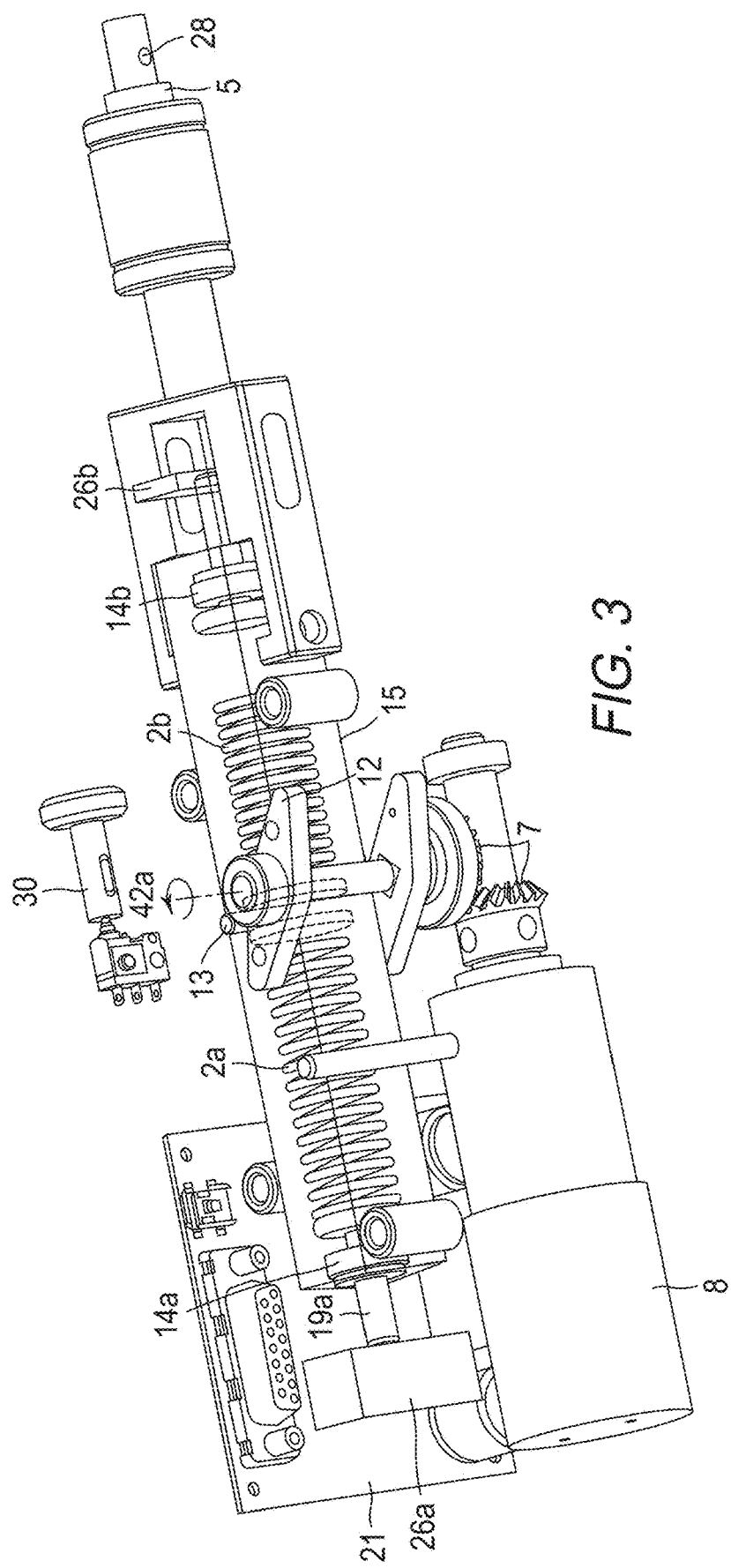
FIG. 3 shows an exemplary embodiment of the tool in FIG. 1 in which after the stored-energy has been released, a launched mass is accelerated towards a point of impact in a forward direction.

FIG. 2 is an exemplary embodiment of the tool in FIG. 1 in which the cam 12 used for actuating the first piston 19a has the first piston 19a "cocked" in the operative position ready for release, or stated another way, the motor 8 rotates the cam 12 in a first direction (viewed as counterclockwise for tautological purposes), as shown by arrow 42a, and compresses the first piston 19a against a first pusher plate 26a, thus storing potential energy within the first spring 2a. In the "cocking phase" the first piston 19a, in combination with the launched mass or striker 15, contacts and is pushed by the cam follower 13, which is driven by the cam 12 in the first direction. As the cam 12 continues to rotate in the first direction, energy stored inside the first spring 2a increases until the cam 12 moves past a release point where it ceases to act on the striker 15 (see FIG. 3, for example). The striker (or launched mass) 15 is now free to travel under the stored potential energy of the first spring 2a. In particular, after a sufficient displacement of the first piston 19a, and after the cam 12 releases the first piston 19a and/or the launched mass 15 combination, the first piston 19a moves in a forward direction, i.e., a direction toward the point of impact, and, at the same time, accelerates the launched mass or striker 15, which is in contact with the face of the first piston 19a. As shown, for example, in FIG. 3, the first piston 19a releases from the striker 15, launching it towards the anvil 5. It was unexpectedly discovered in this invention that the release of the striker 15 from the pusher plate 26a, which essentially creates a portion of free flight during its travel, dramatically reduces the recoil generated and experienced by the surgeons' hands, resulting in a more controllable tool. The striker 15, which has been launched towards the end of the tool that is proximate to the end effector or patient, then percussively impacts a first surface or forward striking surface of the anvil 5, where a maximum displacement of the anvil is less than 10 mm. The impact of the striker 15 on the anvil 5 communicates a forward impact force to an adapter (not shown) and thereby to the broach, chisel, or other orthopedic instrument. The launched mass or striker 15 may be constructed from a suitable material such as steel or any other material having similar properties, lending it to repeated impacting. In an embodiment, a ratio of a weight or mass of the launched mass or striker 15 to a weight or mass of the tool is preferably less than 25%, and the launched mass 15 has an amount of free flight before contact, both factors contributing to a further reduction in the recoil generated.

In a further embodiment it was unexpectedly discovered by increasing the weight or mass of the launched mass in relation to the weight or mass of the anvil that the impact energy was more effectively transferred to the surgical implement. For example, when a ratio of the mass of the launched mass to the mass of the anvil is less than 25%, the resultant transfer efficiency is extremely low, i.e., less than 50% for a typical coefficient of restitution of 0.8. As such, it was found that mass ratios under 50% resulted in the lowest transfer efficiencies of the impact.

In a further embodiment, as illustrated in FIG. 2, for example, as the striker 15 moves in the rearward direction, towards the pusher plate 26a, a bumper 14a functions as a stopper to prevent an end face of the piston 19a from impacting the striker 15. The bumper 14a absorbs the impact of the piston 19a immediately before the launched mass or striker 15 is launched in the forward direction. It was discovered in the course of the invention that without having the piston 19a come to rest on the bumper 14a, excessive wear occurred resulting in failure of the piston 19a. Accordingly, such bumper 14a prevents damage to the spring assembly system, particularly the piston 19a, during repeated operation. The bumper 14a can be one of a plastic or more preferably a rubber or urethane material.

As discussed above, it has been determined by the inventor that his previous designs occasionally resulted in the surgical implement seizing in a biological cavity and the impact of the striker 15 in the rearward direction may be insufficient to dislodge the tool. Further, it was discovered that the rearward force needs to be communicated as a sharp retracting impact in order to dislodge the surgical implement. Accordingly, in the present bidirectional impacting system, there are at least two different impacting surfaces, and, when the tool is being pulled away from the cavity, the striker 15 will impact an alternate surface on the anvil 5 and thereby communicate a rearward force on the anvil 5.

Figure 4:
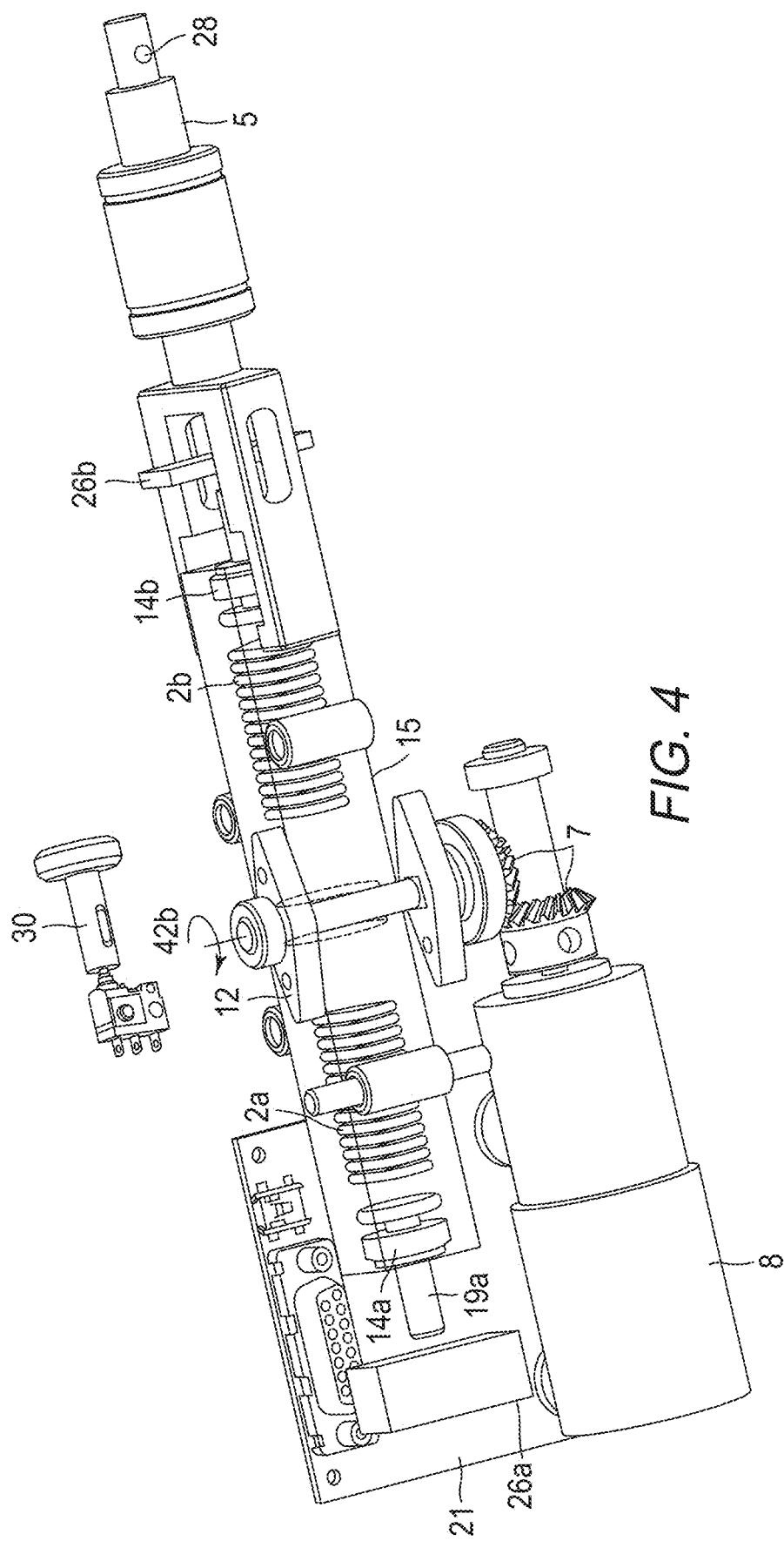
FIG. 4 illustrates a perspective view of an orthopedic impacting tool in accordance with an exemplary embodiment of the present disclosure in which a mechanical spring is used for generating a rearward impact force.
Figure 5:
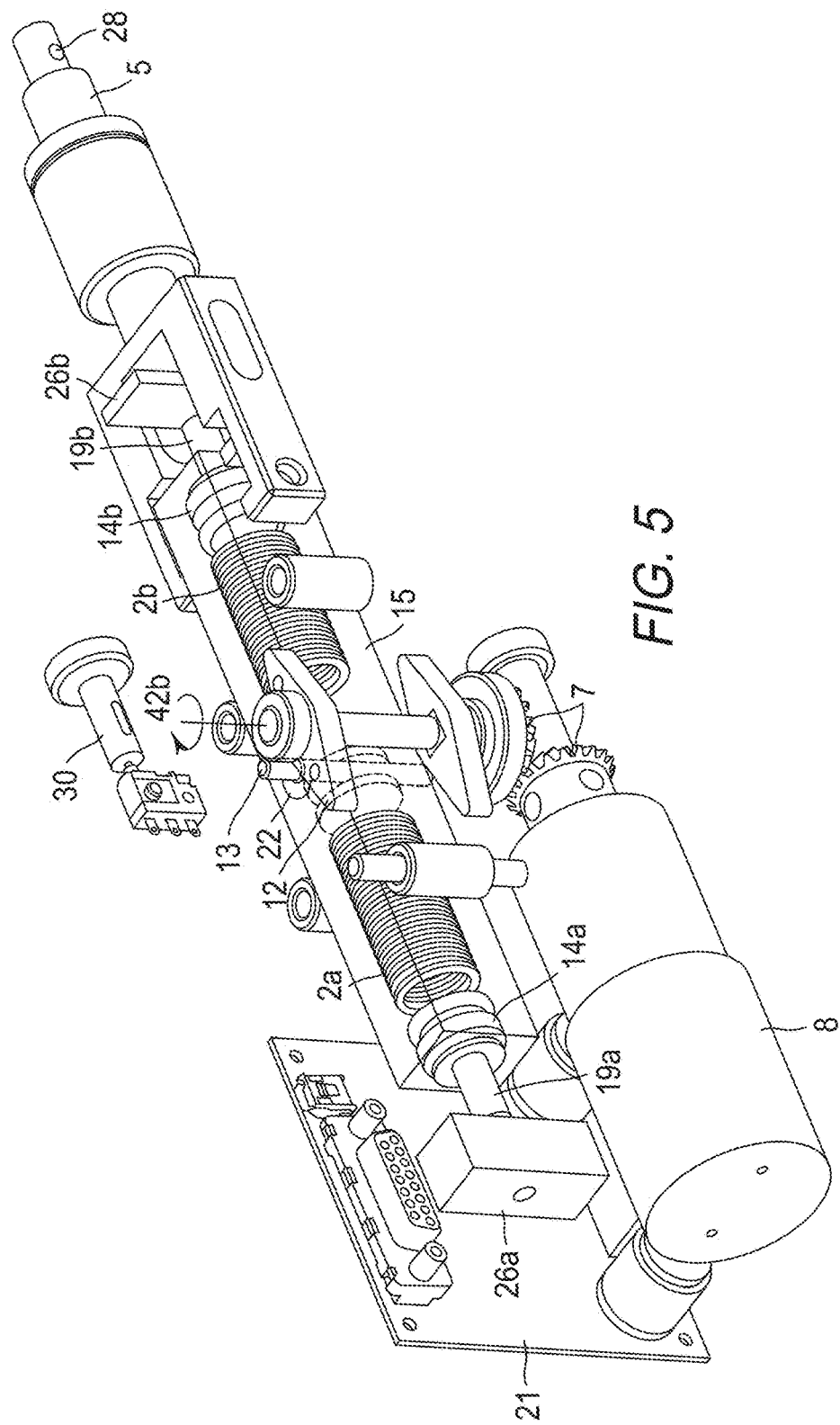
FIG. 5 shows another perspective view of the impacting tool in FIG. 4 from an alternate angle.
Figure 6:
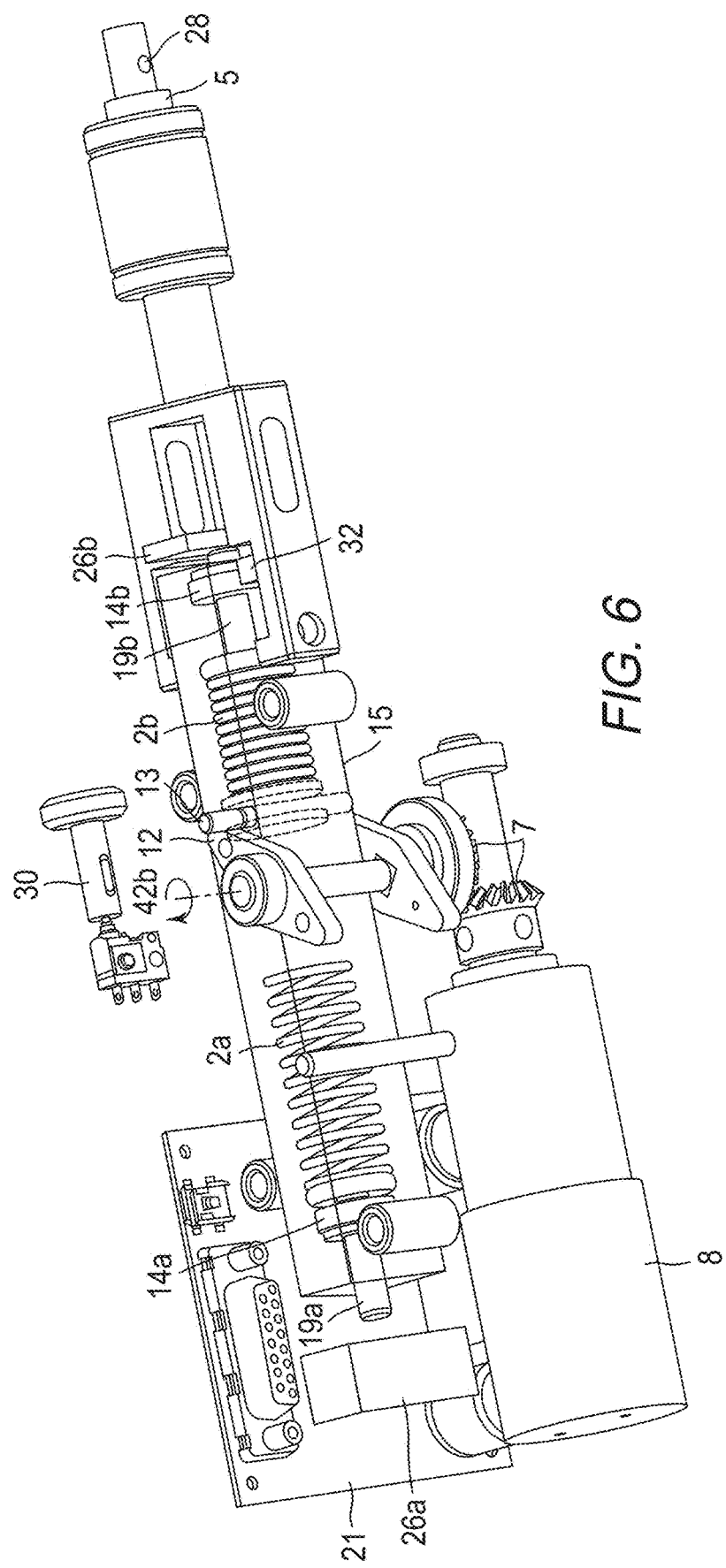
FIG. 6 shows an exemplary embodiment of the tool in FIG. 4 in which the cam of the mechanical spring positions piston in the operative position for release for a rearward impact.
Figure 7:
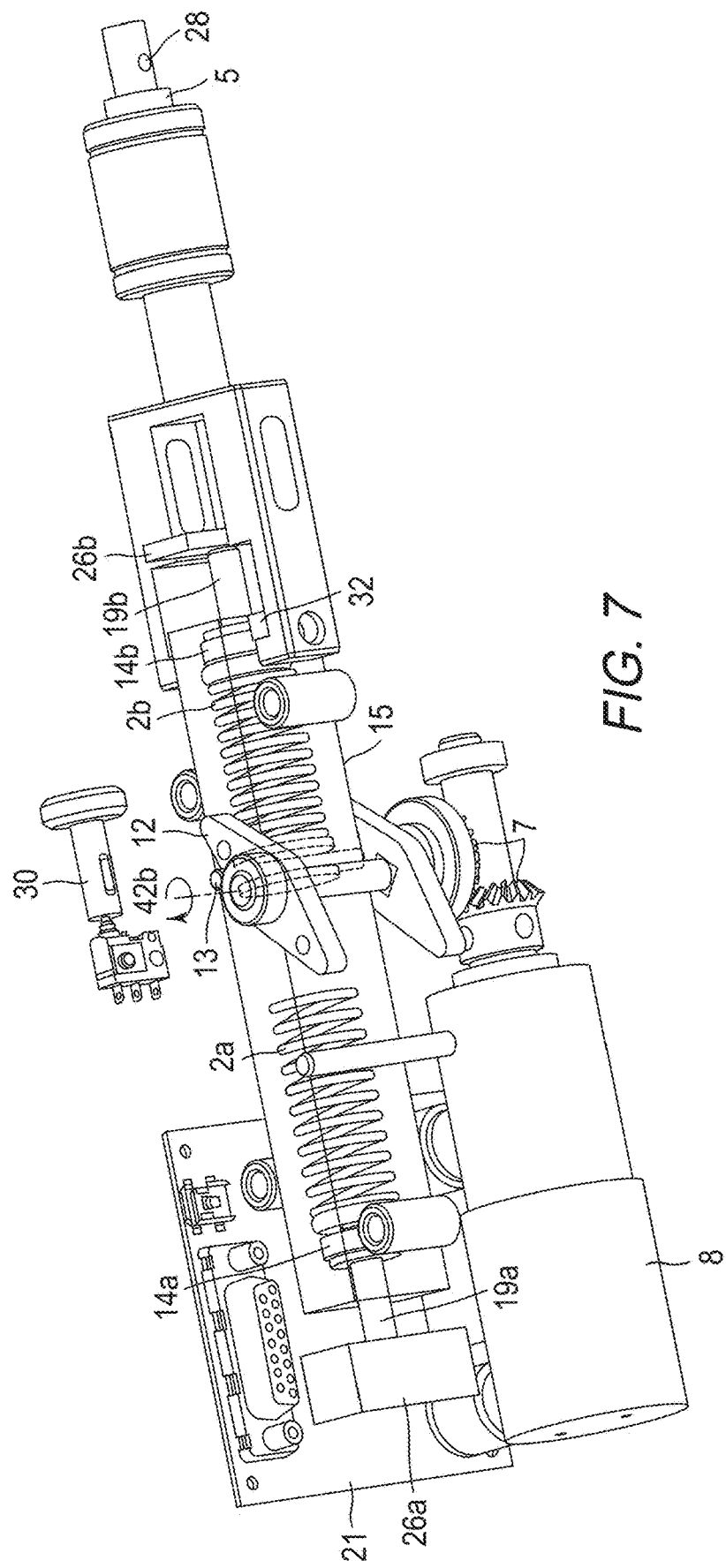
FIG. 7 shows an exemplary embodiment of the tool in FIG. 4 in which after the spring has been released, a launched mass is accelerated towards a point of impact in a rearward direction.

FIGS. 4-7, for example, illustrate a perspective view of an orthopedic impacting tool in accordance with an embodiment of the present disclosure in which the motor and gearbox 8 of the mechanical spring assembly system rotates the cam 12 in a second direction (viewed as clockwise for tautological purposes), as shown by arrow 42b, and launches the mass or striker 15, in order to ultimately generate a rearward impact force. FIG. 4, and similarly FIG. 5, which is another perspective view of the impacting tool shown in FIG. 4 from an alternate angle, illustrates the cam 12 in mid-rotation. As the motor 8 continues to rotate the cam 12 in the second direction, a second spring piston 19b (hereinafter referred to as the "second piston 19b") engages a second spring 2b and is compressed against a second pusher plate 26b, thus storing potential energy within the second spring 2b. The second piston 19b, in turn, is "cocked" in the operative position ready for release (see FIG. 6). In the "cocking phase" the second piston 19b, in combination with the launched mass or striker 15, contacts and is pushed by the cam follower 13. As shown in FIGS. 6 and 7, for example, an end surface of the striker or launched mass 15 includes a pair of extensions or protrusions 32 integral with the launched mass 15 or provided as separate elements bolted to the launch mass 15. As the cam 12 continues to rotate in the second direction, energy stored inside the second spring 2b increases until the cam 12 moves past a release point where it ceases to act on the striker 15 (see FIG. 7, for example). The striker or launched mass 15 is now free to travel under the stored potential energy of the second spring 2b. In particular, after a sufficient displacement of the second piston 19b, and after the cam 12 releases the second piston 19b and/or the launched mass 15 combination, the second piston 19b moves in a rearward direction, i.e., a direction toward the point of impact, and, at the same time, accelerates the launched mass or striker 15, which is in contact with the face of the second piston 19b. As shown, for example, in FIG. 7, the second spring 2b releases from the striker 15, launching it away from the end of the tool that is proximate to the end effector or patient, with the extensions or protrusions 32 of the launched mass 15 impacting an alternate, second or rearward striking surface of the anvil 5, thereby percussively imparting a rearward impact force on the anvil 5, where a maximum displacement of the anvil is less than 10 mm.

Similar to the spring bumper 14a illustrated in FIG. 2 and discussed above, a spring bumper 14b shown in FIG. 4 also functions as a stopper to prevent an end face of the piston 19b from impacting the striker 15, as the piston 19b moves in the forward direction. The bumper 14b absorbs the impact of the piston 19b immediately before the launched mass or striker 15 is launched in the rearward direction. As discussed above, it was discovered in the course of the invention that without having the piston 19b come to rest on the bumper 14b, excessive wear occurred resulting in failure of the piston 19b. Accordingly, such bumper 14b prevents damage to the spring assembly system, particularly the piston 19b, during repeated operation. Similar to bumper 14a, the bumper 14b can be one of a plastic or more preferably a rubber or urethane material.

In an exemplary embodiment, a direction of the force on the anvil 5 is controlled by the user's (such as a surgeon's) manual force on the tool detected by a sensor 28, which can be a positional sensor, on the anvil 5. For example, biasing the tool in the forward direction results in the launched mass or striker 15 being launched forward and gives forward impacting, whereas biasing the tool in the rearward direction results in the striker 15 being launched rearward and gives rearward impacting.

In an embodiment, as the cam 12 assembly completes its stroke, it preferably activates a sensor 22, as shown, for example, in FIG. 5, coupled operatively to a controller 21. The sensor 22 assists in the regulation of the preferred cyclic operation of the cam 12. For example, the sensor 22 may signal the motor 8 to stop such that the cam 12 is at or near a point of minimal potential energy storage. Thus, in one complete cycle, a forward or a rearward impacting force may be applied on the broach, chisel, or other end effector, or on the implant or prosthesis. In a further embodiment, it may be advantageous to stop the cam 12 near a point of maximum potential energy storage to reduce a latency in the surgeons' hands. Latency, as defined, is the time between when the surgeon (or user) activates the orthopedic impacting tool and the tool actually delivers an impact. It has been determined by the inventor that latencies of around 100 milliseconds or less appear essentially as an instantaneous response. By stopping the cam 12 at a point where at least part of the potential energy has been stored, the tool has the effect of near instantaneous release of the potential energy upon actuation of a tool trigger 30. Alternatively, or in addition, a second sensor (not shown) may detect that the broach has stopped advancing for a period of less than 10 seconds, or more preferably, less than 3 seconds during operation, and stops the tool from further impacting. A surgeon will then have to re-initiate the cycle to continue operation.

Figure 8:
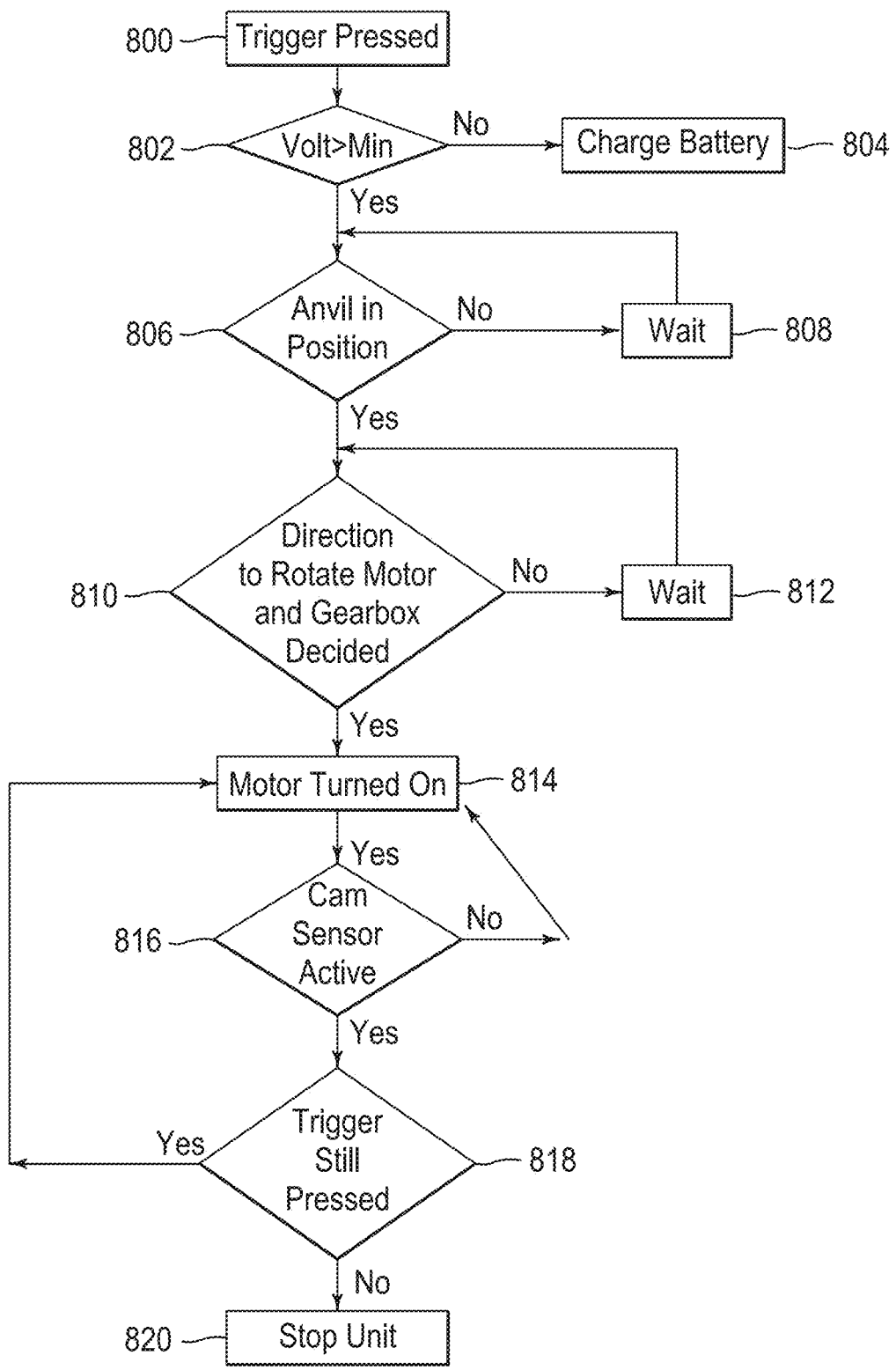
FIG. 8 is an exemplary flow chart illustrating a cyclic operation of the orthopedic impacting tool in accordance with an exemplary embodiment of the present disclosure.

FIG. 8 is an exemplary flow chart illustrating a cyclic operation of an orthopedic impacting tool according to an exemplary embodiment of the present disclosure. At the start of a cycle, a trigger is pressed in step 800 and it is first determined in step 802 whether the orthopedic impacting tool is charged and ready for use. If a voltage of a local power source, such as a battery, is less than a threshold minimum, then the battery is set to charge in step 804. If the voltage of the battery is greater than the threshold minimum, then it is next determined in step 806 whether an anvil and/or broach or other surgical attachment is correctly positioned relative to a cavity of the patient's bone. If the anvil and/or the broach or other surgical attachment is correctly positioned, the operation moves on to step 810; otherwise, the system waits until the position is corrected in step 808. Next, in step 810, it is determined whether a decision has been made as to which direction to rotate the motor and gearbox based on whether the tool is being used to generate a forward impact force or a rearward impact force. If the rotation direction has been decided, then the motor and gearbox combination starts rotating in step 814 in order to complete an impact cycle; otherwise, the system waits until the rotation direction has been determined in step 812. Once the motor gearbox completes an impact cycle, step 816 determines whether a cam sensor has been activated. If the sensor has been activated, then the process proceeds to step 818 to determine whether the trigger is still maintained; otherwise, the process returns to step 814 to allow the motor to continue rotating until the cam sensor has been activated. If a trigger is maintained in step 818, then the operation cycles back to step 814 where the motor continues to rotate, causing the tool to continue generating impacts; otherwise, the operation of the orthopedic impacting tool ceases at step 820.

The controller 21 preferably operates with firmware implementing the cyclic operation described in FIG. 8, which results in the orthopedic impacting tool being able to generate a repeatable, controllable impacting force. The controller 21 can include, for example, intelligent hardware devices, e.g., any data processor, microcontroller or FPGA device, such as those made by Intel® Corporation (Santa Clara, Calif.) or AMD® (Sunnyvale, Calif.). Other type of controllers can also be utilized, as recognized by those skilled in the art.

Advantageously, the dual piston and spring assembly system does not need or use a detent or a magnet for generating a higher energy impact. The impact energy output from the stored-energy drive system is between 1 to 10 joules. In the present bidirectional impacting system the dual piston and spring assembly mechanism is approximately 80% efficient in the rearward direction compared to prior designs, which were about 20% efficient, and more preferably at least 60% efficient. For example, in previous designs, the forward impact force generated approximately 3.5 J of energy, whereas the rearward impact force generated 0.4 J of energy, resulting in a loss of nearly 80% of the energy.

Further, it was unexpectedly discovered that by keeping the compression ratio of the spring to less than 50% of its free length, and more preferably less than 30%, that spring life and impact consistency were maximized. One unexpected effect was generating much more consistent impacts between the striker 15 and the anvil 5, which was a result of the spring not permanently deforming. Indeed, the consistency of the impacts, as generated by the gas or mechanical spring, was found to be within +/−10% of the nominal design value since the impact energy was not subject to atmospheric pressure variations, as it was in the inventor's prior inventions.

The tool may further facilitate controlled continuous impacting, which impacting is dependent on a position of the trigger switch 30 operatively coupled to the power source or motor, for example. For such continuous impacting, after the trigger switch is activated, and depending on the position of the trigger switch 30, the tool may go through complete cycles at a rate proportional to the position of the trigger switch, for example. Thus, in either the single impact or continuous impacting operational modes, the creation or shaping of the surgical area is easily controlled by the surgeon.

As discussed previously, the tool is capable of varying the amount of impact energy per cycle by way of, for example, choosing an appropriate internal pressure for a replaceable gas spring cartridge (such as spring cartridge 900 of FIG. 9) or a different gauge spring for the stored-energy drive system. The gas spring cartridge 900 preferably has an internal pressure of 100 psi, more preferably, between 300 and 3000 psi. Further, the gas spring cartridge 900 may have a pressure release mechanism which releases the pressure at any temperature above 100° C. It will be appreciated that since the drive mechanism for imparting potential energy into the gas spring is a fixed stroke, different impact energies can be obtained in any given surgery by simply using a gas spring cartridge with a different pressure. In a further embodiment, an element, such as a linear cam, can be used to vary the amount of compression in the stored-energy drive system by changing a location of the pusher plate, for example. By controlling the impact energy the tool can avoid damage caused by uncontrolled impacts or impacts of excessive energy.

Figure 9:
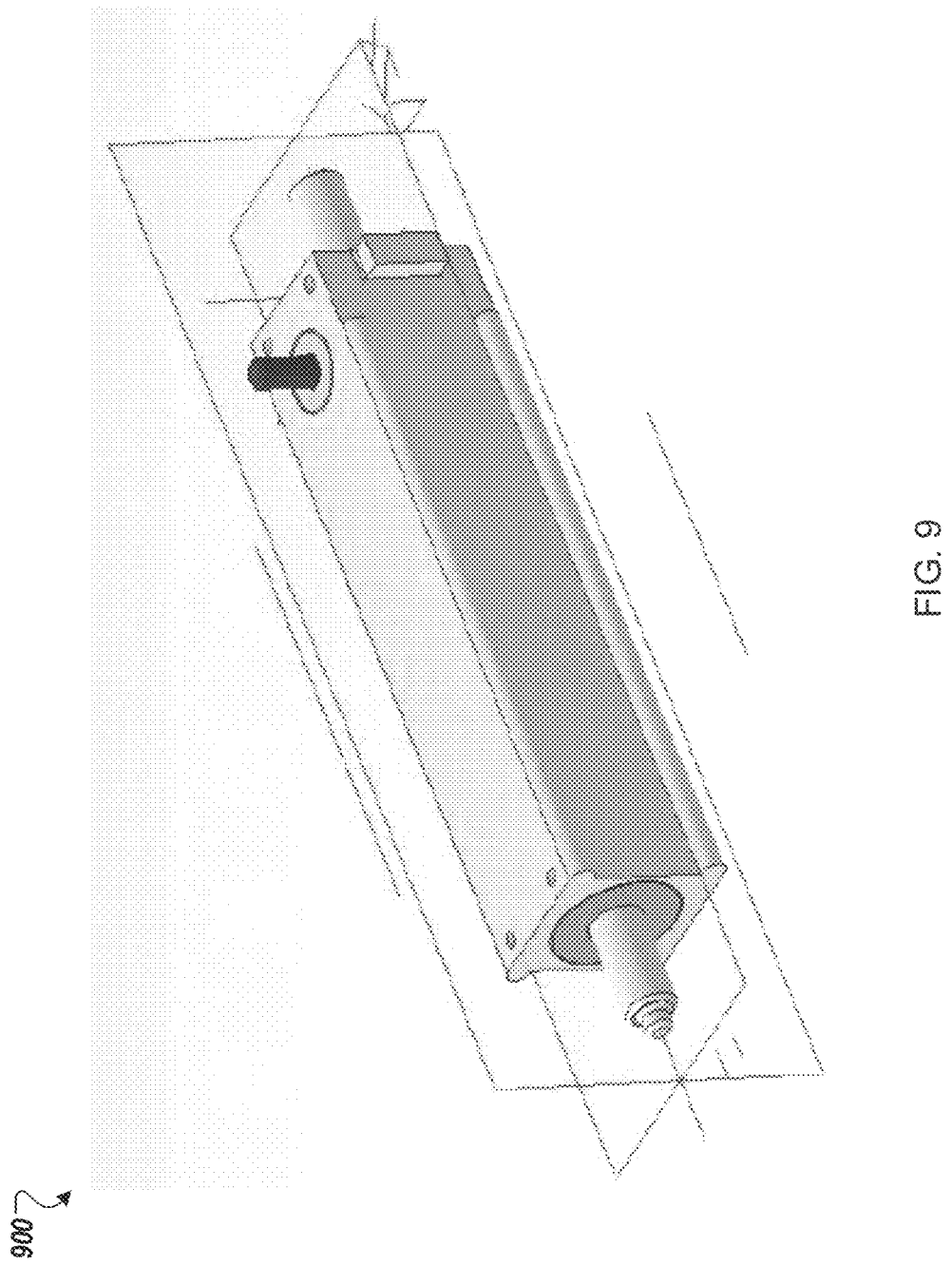
FIG. 9 illustrates an exemplary embodiment of a replaceable spring cartridge usable in an orthopedic impacting tool in accordance with an exemplary embodiment of the present disclosure.

In another embodiment, replaceable gas spring cartridges such as the spring cartridge 900 of FIG. 9 are presterilized and delivered to a surgeon in a sealed container, such as a bag. This allows the surgeon to identify any gas spring cartridges that are leaking, as the bag may be inflated due to the leaking gas.

In a further embodiment, the tool may further be designed to facilitate extraction of well-fixed implants or "potted" broaches. Such embodiment rotates the cam 12 in the second, clockwise direction 42b and launches the mass or striker 15 such that the movement of the striker 15 is away from the patient, causing a retraction or rearward force on the anvil 5.

The tool may further include a compliance element (not shown) inserted between the striker 15 and the anvil 5. Preferably, the compliance element is a resilient material that recovers well from impact and imparts minimal damping on the total energy. As an example, a urethane component could be inserted at the interface where the striker 15 impacts the anvil 5. In a further embodiment, the compliance element may be inserted in such a fashion that it only reduces the impact force in the forward direction and does not affect the desire for a sharp impact force in the rearward direction. This type of compliance element can limit the peak force during impact to preclude such peaks from causing fractures in the patient's bone, yet maintain the high peak force necessary to be able to retract stuck broaches or other surgical implements.

In a still further embodiment, it is understood that the impactor could be coupled to a robot, for example, thus potentially eliminating the need for a portable power source (battery) and or hand grip on the tool.

In a further embodiment, the coupling of the adapter (not shown) to the tool may comprise a linkage arrangement or other adjustment mechanisms known in the art such that the position of the broach, chisel or other end effector can be modified without requiring the surgeon to rotate the tool. The orthopedic tool disclosed herein provides various advantages over the prior art. It facilitates controlled impacting at a surgical site, which minimizes unnecessary damage to a patient's body and allows precise shaping of an implant or prosthesis seat. The tool also allows the surgeon to modulate the direction, force, and frequency of the impacts, which improves the surgeon's ability to manipulate and control the tool. For example, the orthopedic tool can be used solely for retraction purposes depending on the surgical procedure being performed. Similarly, the tool can be customized to have different forward and reverse impact forces. In a mechanical spring assembly system, for example, different gauge springs can be used for forward and reverse impact. The force and compliance control adjustments of the impact settings allow a surgeon to set the force of impact according to a particular bone type or other profile parameter of a patient. Further, the improved efficiency and reduced linear motion converter loads allow use of smaller batteries and lower cost components. The tool thereby enables proper seating or removal of the prosthesis or implant into or out of an implant cavity. Further, the piston and spring assembly provides a simple means for adjusting the impact energy for a particular surgery. Additionally, since the spring assembly is essentially governed by the mechanical properties of the spring, such as the deflection, preload and spring constants, the resulting tool imparts a predictable impact energy independent of the operational speed. Furthermore, in one embodiment in which the gas spring cartridge is replaceable, elements subject to high wear, such as seals and pistons, can be replaced in each surgery, resulting in a more robust, long life tool and reducing points of failure.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. A surgical impacting tool, comprising:
 a piston configured to be compressed and decompressed;
 a spring element configured to store potential energy therein in response to the compression of the piston, and the spring element being configured to release the potential energy in response to the decompression of the piston;
 an electronic controller configured to control storage and release of energy output from the spring element;
 an orthopedic end effector;
 an anvil configured to couple to a surgical implement comprising the orthopedic end effector; and
 a launched mass configured to communicate a striking force to the anvil in response to the release of the potential energy and to the orthopedic end effector coupled to the anvil.

2. The surgical impacting tool of claim 1, wherein the anvil has a first impact surface and a different second impact surface, and
 wherein the launched mass is operable to impact the first impact surface for generating a forward impact force and the second impact surface for generating a rearward impact force.

3. The surgical impacting tool of claim 2, wherein a direction of impacting is controlled by a biasing force applied to the tool by a manipulator,
 wherein the biasing force is configured to alter a position of the anvil in a direction toward a biological object and cause the launched mass to impact the first impact surface, and wherein the biasing force is configured to alter the position of the anvil in a direction away from the biological object and cause the launched mass to impact the second impact surface.

4. The surgical impacting tool of claim 3, further comprising a mount interface, wherein:
the manipulator is a robot; and
the biasing force is applied by the robot via the mount interface.

5. The surgical impacting tool of claim 3, further comprising a hand grip, wherein:
the manipulator is a human operator; and
the biasing force is manually applied by the human operator via the hand grip.

6. The surgical impacting tool of claim 3, wherein the spring element includes a replaceable cartridge.

7. The surgical impacting tool of claim 2, wherein an impact of the rearward impact force is configured to be at least 60% of the forward impact force.

8. The surgical impacting tool of claim 2, further comprising:
a compliance element inserted between the launched mass and the anvil configured to distribute at least one of the forward impact force and the rearward impact force to the first and second impact surfaces of the anvil.

9. The surgical impacting tool of claim 1, wherein the spring element includes one of a mechanical, gas, or elastomeric spring.

10. The surgical impacting tool of claim 1, wherein a ratio of a mass of the launched mass to a mass of the anvil is at least 50%.

11. The surgical impacting tool of claim 1, wherein a maximum displacement of the anvil is less than 10 mm relative to a main portion of the surgical impacting tool.

12. The surgical impacting tool of claim 1, wherein the energy output from the stored-energy drive mechanism is configured to be less than 8 joules.

13. The surgical impacting tool of claim 1, wherein:
rotation of a cam in a first direction is configured to compress the piston; and
continued rotation of the cam in the first direction is configured to release the potential energy.

14. The surgical impacting tool of claim 13, wherein:
rotation of the cam in a second direction opposite to the first direction is configured to compress the piston; and
continued rotation of the cam in the second direction is configured to release the potential energy.

15. The surgical impacting tool of claim 14, further comprising a sensor configured to sense a position of the cam and configured to communicate the sensed position to the controller for controlling the rotation of the cam in the first and second directions.

16. The surgical impacting tool of claim 14, wherein:
the spring element includes first and second spring elements;
the rotation of the cam in the first direction is configured to cause the first spring element to be compressed and decompressed; and
the rotation of the cam in the second direction is configured to cause the second spring element to be compressed and decompressed.

17. The surgical impacting tool of claim 16, wherein latency between activation and the subsequent impact is configured to be less than 100 milliseconds.

18. The surgical impacting tool of claim 1, wherein the controller, after releasing energy to produce the striking force, is configured to stop the cam in a position selected to maximize potential energy storage, thereby reducing latency of a subsequent impact.

19. The surgical impacting tool of claim 1, wherein the decompression of the piston is configured to cause unconstrained displacement of the launched mass before communicating the striking force to the anvil.

20. The surgical impacting tool of claim 1, further comprising at least one bumper contained within the launched mass, the bumper being configured to moderate the striking force.

21. The surgical impacting tool of claim 1, further comprising a portable power source.

22. The surgical impacting tool of claim 1, wherein a compression ratio of the spring element is less than 50% of a free length of the spring element.

23. The surgical impacting tool of claim 1, further comprising an adapter coupled to the anvil, the adapter being configured to accept the surgical implement.

24. The surgical impacting tool of claim 1, wherein:
the piston is configured to be compressed in response to rotation of a cam in a first direction and to be decompressed in response to continued rotation of the cam in the first direction; and
after the piston is decompressed in response to continued rotation of the cam in the first direction, the piston is configured to be compressed in response to rotation of the cam in a second, opposite direction and configured to be decompressed in response to continued rotation of the cam in the second direction.

25. The surgical impacting tool of claim 24, wherein:
the anvil is configured to couple to the surgical implement at a forward end of the anvil; and
the decompression of the piston in response to continued rotation of the cam in the first direction is configured to cause the surgical implement coupled to the anvil to move in a forward direction relative to a patient; and
the decompression of the piston in response to continued rotation of the cam in the second direction is configured to cause the surgical implement coupled to the anvil to move in a rearward direction relative to the patient.

26. The surgical impacting tool of claim 1, wherein the piston is configured to be compressed against a plate and decompressed away from the plate.

27. The surgical impacting tool of claim 1, wherein the spring element includes a mechanical spring.

28. A surgical impacting tool, comprising:
a cam configured to rotate;
a cam follower operatively coupled to the cam;
first and second spring elements operatively coupled to the cam, the cam follower being positioned between a proximal end of the first spring element and a distal end of the second spring element, the rotation of the cam in a first direction being configured to store energy in the first spring element and to thereafter release energy stored in the first spring element, and the rotation of the cam in a second, opposite direction being configured to store energy in the second spring element and to thereafter release energy stored in the second spring element;
an electronic controller configured to control rotation of the cam;
an orthopedic end effector;
an anvil configured to couple to a surgical implement comprising the orthopedic end effector; and
a mass operatively coupled to the first and second spring elements and configured to communicate a striking force to the anvil in response to decompression of each of the first and second spring elements and to the orthopedic end effector coupled to the anvil.

29. The surgical impacting tool of claim 28, wherein:
the anvil is configured to couple to the surgical implement at a distal end of the anvil;
the decompression of the first spring element in response to continued rotation of the cam in the first direction is configured to cause the surgical implement coupled to the anvil to move in a distal direction relative to a patient; and
the decompression of the second spring element in response to continued rotation of the cam in the second direction is configured to cause the surgical implement coupled to the anvil to move in a proximal direction relative to the patient.

30. The surgical impacting tool of claim 28, wherein each of the first and second spring elements includes a mechanical spring.

31. The surgical impacting tool of claim 28, wherein:
the decompression of the first spring element is configured to cause the mass to impact a first impact surface of the anvil;
the decompression of the second spring element is configured to cause the mass to impact a second, different impact surface of the anvil;
a direction of impacting is configured to be controlled by a biasing force applied to the tool by a manipulator;
the biasing force is configured to alter a position of the anvil in a direction toward a biological object and cause the mass to impact the first impact surface; and
the biasing force is configured to alter a position of the anvil in a direction away from the biological object and cause the mass to impact the second impact surface.

32. The surgical impacting tool of claim 28, wherein:
rotation of the cam in the first direction is configured to compress the first spring element;
continued rotation of the cam in the first direction is configured to release the energy stored in the first spring element;
rotation of the cam in a second direction opposite to the first direction is configured to compress the second spring element, and
continued rotation of the cam in the second direction is configured to release the energy stored in the second spring element.

* * * * *